United States Patent
Hsu et al.

(10) Patent No.: US 8,958,865 B2
(45) Date of Patent: Feb. 17, 2015

(54) LESION PHANTOM PREVENTING IMAGING CONTRAST AGENTS OR MEDICINE FROM OVERFLOW WHEN LESION PHANTOM CAVITY IS FILLED

(75) Inventors: Shiang-Lin Hsu, Taoyuan County (TW); Yu-Ching Ni, Taoyuan County (TW); Meei-Ling Jan, Taoyuan County (TW)

(73) Assignee: Institute of Nuclear Energy Research Atomic Energy Council, Executive Yuan, Taoyuan County (TW)

( * ) Notice: Subject to any disclaimer, the term of this patent is extended or adjusted under 35 U.S.C. 154(b) by 320 days.

(21) Appl. No.: 13/422,225

(22) Filed: Mar. 16, 2012

(65) Prior Publication Data

US 2013/0091966 A1 Apr. 18, 2013

(30) Foreign Application Priority Data

Oct. 14, 2011 (TW) .............................. 100137371 A

(51) Int. Cl.
*A61B 6/03* (2006.01)
*G01R 33/48* (2006.01)
*A61B 6/00* (2006.01)

(52) U.S. Cl.
CPC ............ *A61B 6/037* (2013.01); *G01R 33/4808* (2013.01); *G01R 33/481* (2013.01); *A61B 6/481* (2013.01); *A61B 6/583* (2013.01)
USPC .......................................... 600/411; 324/321

(58) Field of Classification Search
USPC .......... 324/300–322; 600/407–435, 561–567; 382/128–131; 434/272, 267; 73/866.4, 73/41.2; 436/8, 80; 606/130; 137/107, 414
See application file for complete search history.

(56) References Cited

U.S. PATENT DOCUMENTS

| | | | | |
|---|---|---|---|---|
| 3,283,772 A * | 11/1966 | Ensign | ......................... | 137/107 |
| 3,350,919 A * | 11/1967 | Mucci et al. | ................... | 73/41.2 |
| 3,527,172 A * | 9/1970 | Morgan et al. | ................ | 137/414 |
| 5,549,616 A * | 8/1996 | Schulte et al. | ................ | 606/130 |
| 5,797,924 A * | 8/1998 | Schulte et al. | ................ | 606/130 |
| 6,447,462 B1 * | 9/2002 | Wallace et al. | ............... | 600/561 |
| 6,954,068 B1 * | 10/2005 | Takamori et al. | ............ | 324/318 |
| 6,994,315 B2 * | 2/2006 | Ryan et al. | .................. | 251/149.6 |
| 7,462,488 B2 * | 12/2008 | Madsen et al. | ..................... | 436/8 |
| 7,693,567 B2 * | 4/2010 | Tsonton et al. | ............... | 600/411 |
| 7,862,517 B2 * | 1/2011 | Tsonton et al. | ............... | 600/567 |
| 8,480,407 B2 * | 7/2013 | Campbell et al. | ............. | 434/272 |
| 8,535,061 B2 * | 9/2013 | Boutchko et al. | ............. | 434/267 |
| 2004/0067591 A1 * | 4/2004 | Madsen et al. | ..................... | 436/8 |
| 2005/0227364 A1 * | 10/2005 | Madsen et al. | .................. | 436/80 |

(Continued)

*Primary Examiner* — Melissa Koval
*Assistant Examiner* — Tiffany Fetzner
(74) *Attorney, Agent, or Firm* — WPAT, PC; Justin King

(57) ABSTRACT

A lesion phantom is disclosed, which is a spherical ball having a cavity formed therein for housing contrast agents or medicines, and is enabled for the quantitative evaluation of a medical image in drug development and evaluation. In an embodiment, the cavity of the lesion phantom is coupled to a tapering ring and is configured to be sealed by a silicon plug, in order to ensure that contrast agents or medicines can be fed into the cavity easily and conveniently without causing any problem, such as overflowing, a bubble residue problem, radioactive contamination, etc. Moreover, by the arrangement of a retractable fixing bar, the positioning of the lesion phantom can be adjusted flexibly at will, and additionally by the tapering of the tapering ring, the lesion phantom can be prevented from being damaged by any extreme, sudden, unjust, or improper force exerted, and thus the lifespan of the lesion phantom can be prolonged.

4 Claims, 7 Drawing Sheets

(56) References Cited

U.S. PATENT DOCUMENTS

| | | | |
|---|---|---|---|
| 2005/0277829 A1* | 12/2005 | Tsonton et al. | 600/423 |
| 2007/0167736 A1* | 7/2007 | Dietz et al. | 600/411 |
| 2008/0015429 A1* | 1/2008 | Tsonton et al. | 600/414 |
| 2009/0281453 A1* | 11/2009 | Tsonton et al. | 600/567 |
| 2010/0041005 A1* | 2/2010 | Campbell et al. | 434/267 |
| 2010/0167251 A1* | 7/2010 | Boutchko et al. | 434/267 |
| 2013/0091966 A1* | 4/2013 | Hsu et al. | 73/866.4 |
| 2013/0231586 A1* | 9/2013 | Tsonton et al. | 600/567 |

* cited by examiner

41: external thread
611: internal thread
61: first annular section
62: second annular section
63: third annular section

LESION PHANTOM PREVENTING IMAGING CONTRAST AGENTS OR MEDICINE FROM OVERFLOW WHEN LESION PHANTOM CAVITY IS FILLED

FIELD OF THE INVENTION

The present invention relates to a technique for evaluating a medical image, and more particularly, to a spherical lesion phantom having a cavity formed therein for housing contrast agents or medicines, being is enabled for the quantitative evaluation of a medical image, such as a SPECT image, a PET image or a MRI image, in drug development and evaluation.

BACKGROUND OF THE INVENTION

Medical molecular imaging originated from the field of radio pharmacology due to the need to better understand the fundamental molecular pathways inside organisms in a non-invasive manner. In a process of molecular imaging, probes known as biomarkers are used to help image particular targets or pathways. Biomarkers interact chemically with their surroundings and in turn alter the image according to molecular changes occurring within the area of interest. It enables the visualization of the cellular function and the follow-up of the molecular process in living organisms without perturbing them. This ability to image fine molecular changes opens up an incredible number of exciting possibilities for medical application, including early detection and treatment of disease and basic pharmaceutical development. However, no matter it is for the development and evaluation of new drugs using molecular imaging research, or for the evaluation upon the effectiveness of a SPECT system, a PET system, or a MRI system, a good biological phantom is required.

In order to obtain clinically realistic images in a quantitative medical research in drug development and evaluation, anthropomorphic phantoms are generally used and required. Among which lesion phantoms which represent areas of interest are oftentimes the focal points of many quantitative medical evaluations, such as the quantification and assessment of drug absorption rate in lesions, the calibration of medical imaging upon lesions, the evaluation of how the amount of drug absorption can affect the threshold setting in a medical imaging for lesion detection.

There are two types of lesion phantoms currently available on the market. Among which, the type that is referred as "cold phantom" is a phantom formed without contrast agent/medicine reservoir and is generally a solid structure made of a tissue-mimicking material; while another type is referred as "hot phantom", that is a phantom formed with contrast agent/medicine reservoir and is generally a hollow structure made of a tissue-mimicking material. Comparatively, the hot phantom is more flexible in usage as it is able to simulate lesions of different absorption rates, and also can be used as a "cold phantom" while having its cavity to be filled with certain non-active materials.

In any phantom study for quantitatively evaluating and assessing a medical imaging system in drug development and evaluation, the accuracy of lesion signal caused by the hot phantom is most valued since any minute error in the reading of the lesion signal may be of serious consequence in the drug development and evaluation. Accordingly, the accuracy of lesion signal is severely dependent upon the accuracy of the hot phantom, not just in the accuracy relating to the volume of the phantom, but also in the accuracy relating to the amount of contrast agent or medicine that are to be fed into the cavity of the hot phantom. It is noted that a good lesion phantom should be able to be used repetitively while allowing each injection and removal of contrast agent to be performed accurately in volume and with high degree of repeatability. However, such accuracy and good repeatability are not achievable by the phantoms that are currently available on the market. Generally, after several repetitive injections and removals of contrast agent, the probability of signal contamination, i.e. signals being generated at positions where are not expected, or radioactive contamination, i.e. the extravasation of radioactive contrast agent or medicine, is often increased exponentially. In addition, with regard to the positioning of lesion phantom, the usage of those phantoms that are currently available on the market are not flexible in that they are fixed to be secured at only a few specific positions and cannot be changed at will. Furthermore, the internal diameter of the smallest lesion phantoms that are currently available on the market is still 3.95 mm, which is not small enough to be in many medical imaging researches. Thus, the lesion phantoms that are currently available on the market are known to be insufficient in accuracy, ease-of-use, usage flexibility, and reality, and therefore, they are required to be improved.

Please refer to FIG. 4, which is a schematic diagram showing a prior-art breast phantom by Data Spectrum Cooperation. Nevertheless, each lesion phantom 1 in FIG. 4 is still being fixed to one specific position at its corresponding breast that it is not allowed to be changed at will. Please refer to FIG. 5, which is a schematic diagram showing a spherical lesion phantom used in the breast phantom of FIG. 4 that is filled with a contrast agent. In FIG. 5, the spherical lesion phantom 1', being a "hot phantom", can be filled with a contrast agent 8' through injection using a needle. However, it is noted that such spherical lesion phantom 1' sill has problems, e.g. the overflowing of contrast agent 8' is not preventable, as shown in FIG. 6, and also there can be bubbles 9' trapped inside the spherical lesion phantom 1', as shown in FIG. 7. In addition, since the fixing bar 7' is fixedly secured to the sphere 2' of the lesion phantom 1' by screwing the external thread 71' formed on the fixing bar 7' to mate with the internal thread 31' formed inside the extension tube 3' of the sphere 2', such fixing manner can easily cause the residue contrast agent 8' at the interface between the lesion phantom 1' and the external thread 71' to be squeezed and thus overflow. Therefore, the problems including the signal contamination, i.e. signals being generated at positions where are not expected, and radioactive contamination, i.e. the extravasation of radioactive contrast agent, cannot be prevented during the performing of a medical imaging research.

Moreover, as the fixing bar 7' is made of a specific size, especially in length, that it is not adjust able in length, the lesion phantom 1' can only fixed to a specific position inside the breast phantom. In addition, the internal diameter of the sphere 2' of the lesion phantom 1' is about 3.95 mm that it is not able to mimic tumors or lesions smaller than that.

Therefore, it is in need of a lesion phantom capable overcoming the aforesaid shortcomings

SUMMARY OF THE INVENTION

The object of the present invention is to provide a lesion phantom, designed to have a cavity formed thereon to be sealed by the plugging of a silicon plug into an end of a tapering ring which has a smaller opening while allowing both a needle for gas exhaustion and a needle for contrast agent/medicine injection to be inserted therein, and thereby, enabling the internal pressure inside the cavity to equal with the pressure outside the cavity and thus allowing the injection of the contrast agent/medicine to be performed easily without causing any overflow or bubble residue, resulting in that the contrast agent/medicine can be injected into the lesion phantom accurately in a simple operation with good repeatability.

Another object of the invention is to provide a lesion phantom, capable of using a tapering ring that is coupled to a cavity formed inside the sphere of the lesion phantom for enabling bubbles that are being caused during the injection of contrast agent/medicine to concentrate at the neighborhood of the tapering ring, and thereafter, allowing the trapped bubbles to be discharged out of the sphere through the needle for gas exhaustion. Moreover, by the tapering of the tapering ring, the lesion phantom can be prevented from being damaged by any extreme, sudden, unjust, or improper force exerted, and thus the lifespan of the lesion phantom can be prolonged.

Further another object of the invention is to provide a lesion phantom, capable of using the arrangement of a retractable fixing bar for allowing the positioning of the lesion phantom to be adjusted flexibly at will.

Further another object of the invention is to provide a lesion phantom, designed with a sphere, which has a 2 mm internal diameter for satisfying the requirement of a clinical medical imaging research designed for detecting and evaluating small lesions.

To achieve the above objects, the present invention provides a lesion phantom, comprising: a cavity, formed with an opening; a tapering ring, configured with a first ring and a second ring in a manner that the first ring is formed with a diameter larger than that of the second ring while allowing the first ring to be arranged in communication with the opening of the cavity; a screw tube, formed with an external thread at its outer surface, and having an end thereof to be arranged in communication with the second ring of the tapering ring while allowing the screw tube to be formed with an internal diameter larger than the diameter of the second ring; a silicon plug, removably disposed inside the screw tube while allowing an end of the silicon plug to engage with the second ring of the tapering ring; a sleeve, configured with a first annular section, a second annular section and a third annular section in a manner that the first annular section is formed with an internal thread on its inner surface so as to removably mate with the external thread of the screw tube by screwing, the second annular section is arranged for enabling the two ends thereof to connected respectively to the first annular section and the third annular section; and a fixing bar, configured with a first rod and a second rod in a manner that the first rod is formed with a diameter about equal to the internal diameter of the second annular section of the sleeve, and the second rod is formed with a diameter about equal to the internal diameter of the third annular section of the sleeve, while allowing the first rod to fit into the second annular section of the sleeve and simultaneously allowing an end of the second rod that is disposed neighboring to the first rod to be removably inset and fixed inside the third annular section of the sleeve.

In an embodiment of the invention, the cavity is formed as a sphere.

In another embodiment of the invention, the internal diameter of the second annular section is formed tapering from the first annular section toward the third annular section, and consequently, the first rod is formed in a shape conforming to the tapering of the second annular section.

In another embodiment of the invention, the second rod of the fixing bar is substantially a retractable rod.

In another embodiment of the invention, the silicon plug, being formed as a conical cylinder, is disposed for enabling an end thereof that is formed a larger diameter larger than another end thereof to be arranged proximate to the second ring, while allowing the end with the larger diameter to be formed larger than the second ring in diameter.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

The fulfilled functions and structural characteristics of the invention, are shown by the several exemplary embodiments cooperating with detailed description which are now presented.

Figure 1:
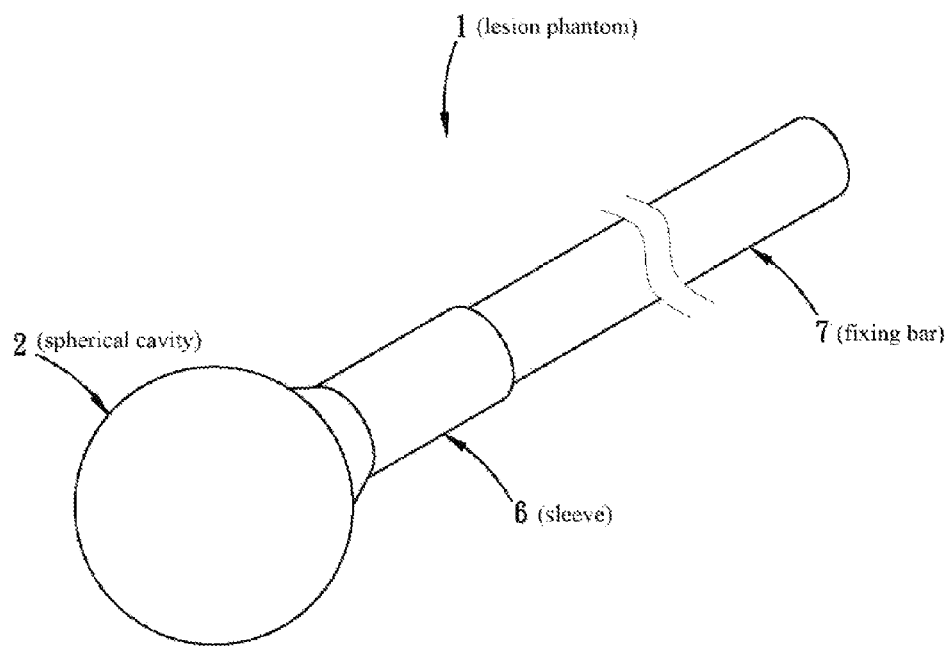
FIG. 1 is a three-dimensional view of a lesion phantom according to an embodiment of the invention.
Figure 2:
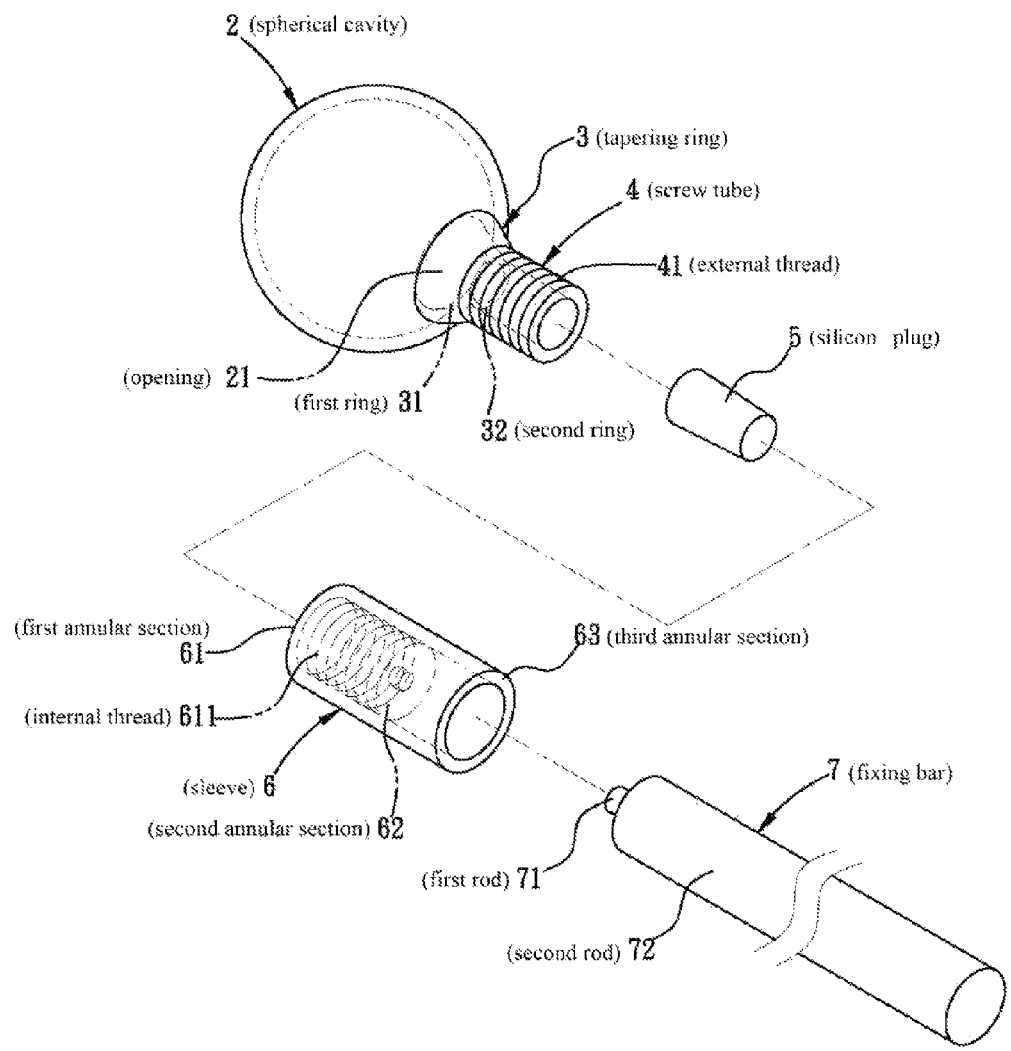
FIG. 2 is an exploded view of FIG. 1.
Figure 3:
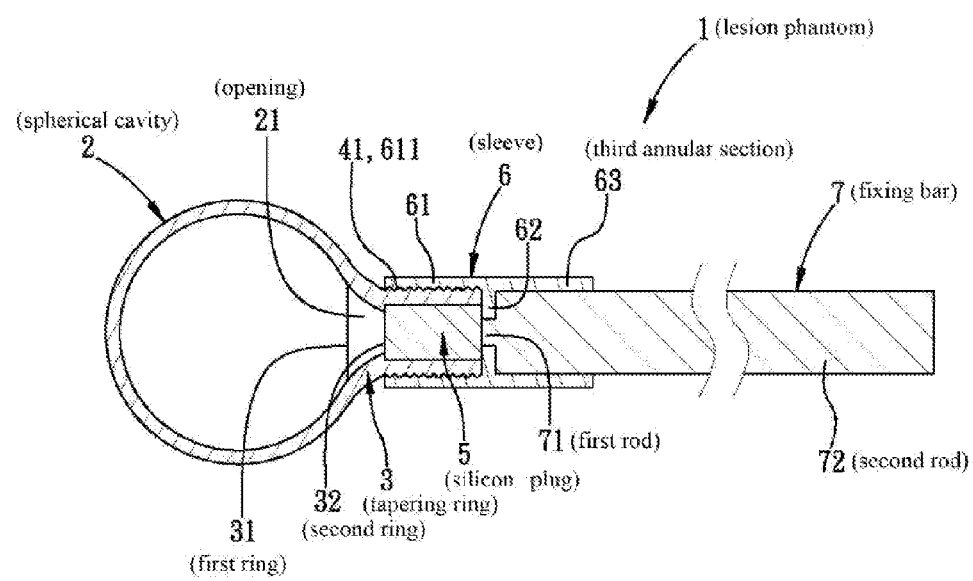
FIG. 3 is a cross sectional view of FIG. 1.
Figure 4:
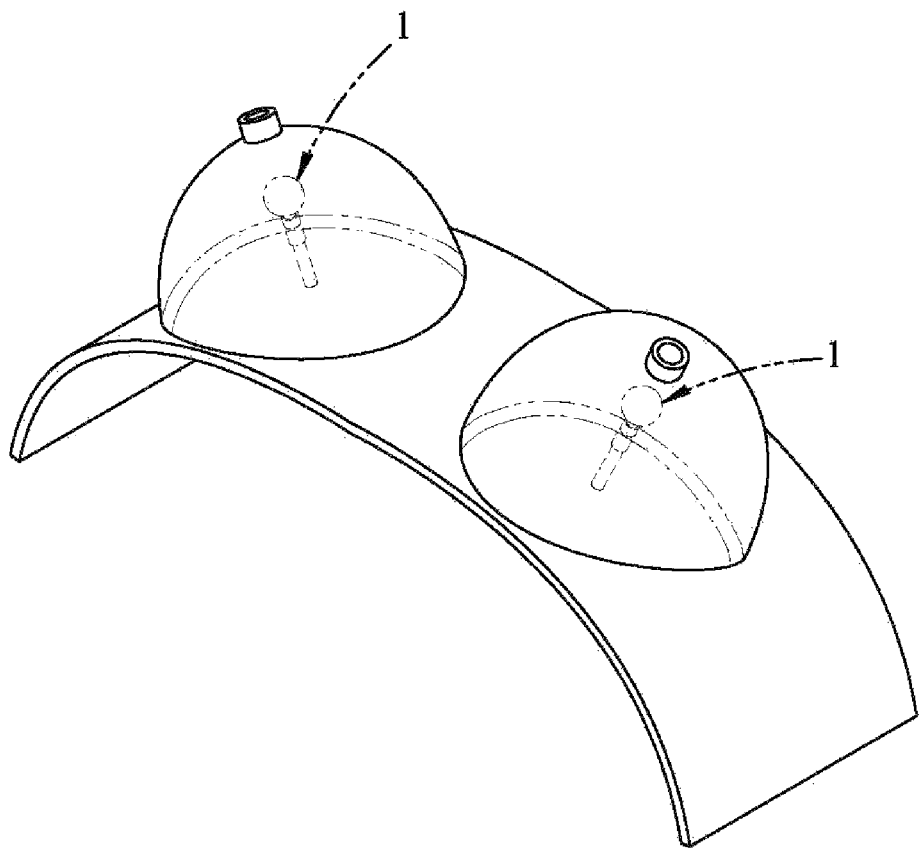
FIG. 4 is a schematic diagram showing a prior-art breast phantom by Data Spectrum Cooperation.
Figure 5:
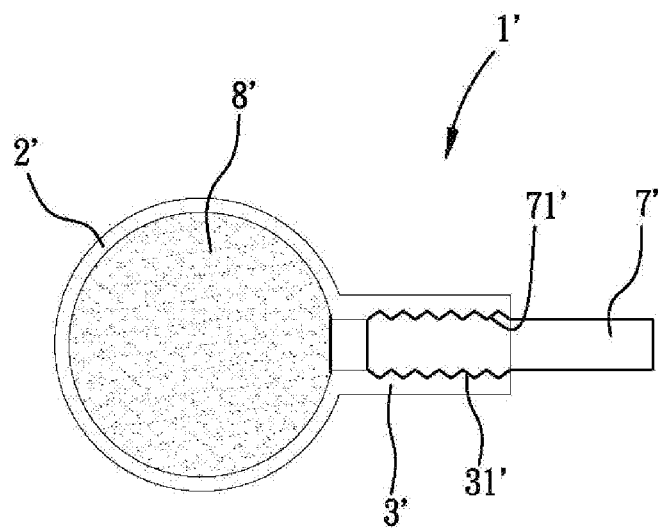
FIG. 5 is a schematic diagram showing a spherical lesion phantom used in the breast phantom of FIG. 4 that is filled with a contrast agent.
Figure 6:
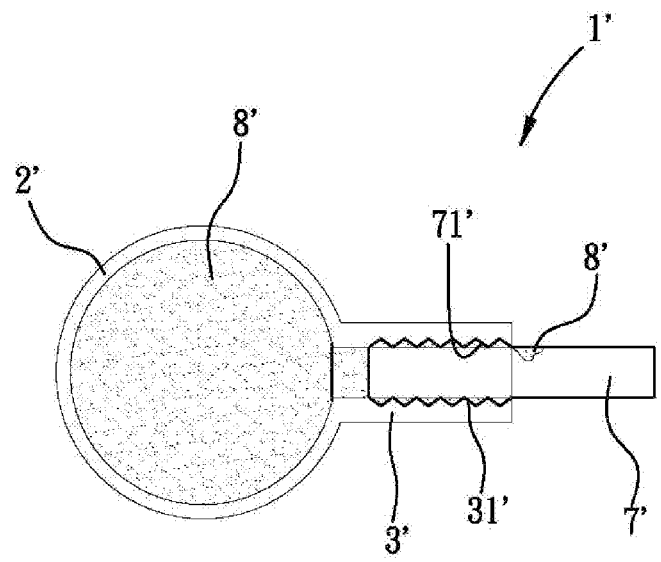
FIG. 6 is a schematic diagram showing a spherical lesion phantom used in the breast phantom of FIG. 4 that is filled with a contrast agent while the contrast agent is overflowing.
Figure 7:
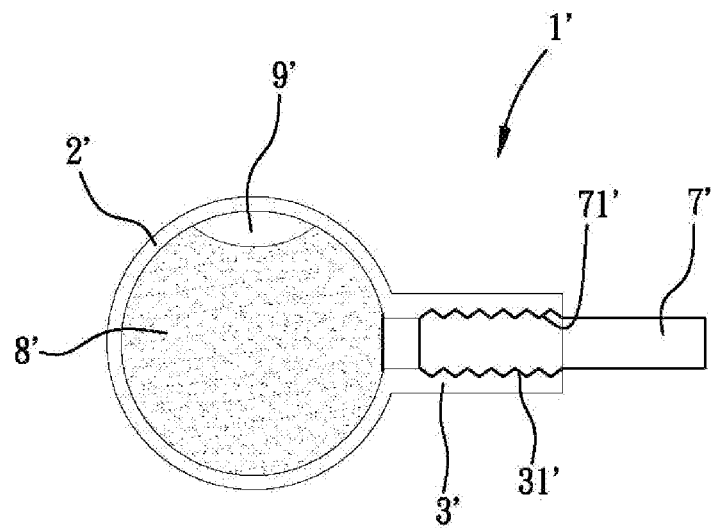
FIG. 7 is a schematic diagram showing a spherical lesion phantom used in the breast phantom of FIG. 4 that is filled with a contrast agent while having bubbles trapped therein.

Please refer to FIG. 1, FIG. 2 and FIG. 3, which are a three-dimensional view of a lesion phantom according to an embodiment of the invention, an exploded view of FIG. 1, and a cross sectional view of FIG. 1.

As shown in FIG. 1, FIG. 2 and FIG. 3, the lesion phantom 1 is composed of a cavity 2, a tapering ring 3, a screw tube 4, a silicon plug 5, a sleeve 6 and a fixing bar 7. In this embodiment, the cavity 2 is formed as a sphere with an opening 21.

The tapering ring 3 is configured with a first ring 31 and a second ring 32 in a manner that the first ring 31 is formed with a diameter larger than that of the second ring 32 while allowing the first ring 31 to be arranged in communication with the opening 21 of the cavity 2.

The screw tube 4 is disposed for enabling an end thereof to be arranged in communication with the second ring 32 of the tapering ring 3, and is formed with an external thread 41 at its outer surface while allowing the internal diameter of the screw tube 4 to be formed larger than the diameter of the second ring 32.

The silicon plug 5 is arranged removably fitting inside the screw tube 4 while allowing an end of the silicon plug 5 to engage with the second ring 32 of the tapering ring 3. Preferably, the silicon plug 5 is formed as a conical cylinder, as shown in FIG. 2. Moreover, the silicon plug 5 is disposed for enabling an end thereof that is formed with a diameter larger than that of another end thereof to be arranged proximate to the second ring 32, while allowing the end with the larger diameter to be formed larger than the second ring 32 in diameter.

The sleeve 6 is configured with a first annular section 61, a second annular section 62 and a third annular section 63 in a manner that the first annular section 61 is formed with an internal thread 611 on its inner surface so as to removably mate with the external thread 41 of the screw tube 4 by screwing, and the second annular section 62 is arranged for enabling the two ends thereof to connected respectively to the first annular section 61 and the third annular section 63.

The fixing bar 7 is configured with a first rod 71 and a second rod 72 in a manner that the first rod 71 is formed with a diameter about equal to the internal diameter of the second annular section 62 of the sleeve 6, and the second rod 72 is formed with a diameter about equal to the internal diameter of the third annular section 63 of the sleeve 6, while allowing the first rod 71 to fit into the second annular section 62 of the sleeve 6 and simultaneously allowing an end of the second rod 72 that is disposed neighboring to the first rod 71 to be removably inset and fixed inside the third annular section 63 of the sleeve 6. Moreover, the second rod 72 of the fixing bar 7 is substantially a retractable rod.

In addition, the internal diameter of the second annular section 62 is formed tapering from the first annular section 61 toward the third annular section 61, and consequently, the first rod 71 of the fixing bar 7 is formed in a shape conforming to the tapering of the second annular section 62.

Operationally, by the arrangement of the silicon plug 5, the lesion phantom 1 can allow both a needle for gas exhaustion and a needle for contrast agent/medicine injection to be inserted therein simultaneously, and thereby, enable the internal pressure inside the cavity to equal with the pressure outside the cavity so that the injection of the contrast agent/medicine can be performed easily without causing any overflow or bubble residue. In this invention, for preventing the silicon plug 5 from falling off, the silicon plug 5 is disposed for enabling an end thereof to be engaged and thus fixed by the tapering of the tapering ring 3 while allowing another end thereof to abut against and thus be fixed by the second annular section 62 and the first rod 71 of the fixing bar 7. Accordingly, after the silicon plug 5 is aged, it can be removed and replaced simply by removing the sleeve 6 and the fixing bar 7, which is pretty simple. In addition, by coupling the opening 21 of the cavity 2 to the tapering ring 3, bubbles that are being caused during the injection of contrast agent/medicine will tend to concentrate at the neighborhood of the tapering ring 3 this tendency will allow the trapped bubbles to be discharged out of the cavity 2 through the use of the needle for gas exhaustion. Moreover, by the tapering of the tapering ring, the lesion phantom can be prevented from being damaged by any extreme, sudden, unjust, or improper force exerted, and thus the lifespan of the lesion phantom can be prolonged. In addition, by the arrangement of the sleeve 6, which permits and allows the retractable fixing bar 7 to be coupled with and received inside the sleeve 6, the positioning of the lesion phantom 1 can be adjusted flexibly at will.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A lesion phantom, comprising:
    a cavity, formed with an opening;
    a tapering ring, configured with a first ring and a second ring in a manner that the first ring is formed with a diameter larger than that of the second ring while allowing the first ring to be arranged in communication with the opening of the cavity;
    a screw tube, formed with an external thread at its outer surface, and having an end thereof to be arranged in communication with the second ring of the tapering ring while allowing the screw tube to be formed with an internal diameter larger than the diameter of the second ring;
    a silicon plug, formed as a conical cylinder, and removably disposed inside the screw tube while allowing an end of the silicon plug to engage with the second ring of the tapering ring, wherein the silicon plug is disposed in order to enable an end thereof that is formed with a diameter larger than that of another end thereof to be arranged adjacent the second ring, while allowing the end with the larger diameter to be formed larger than the second ring in diameter;
    a sleeve, configured with a first annular section, a second annular section and a third annular section in a manner that the first annular section is formed with an internal thread on its inner surface in order to removably mate with the external thread of the screw tube by screwing, and the second annular section is arranged in order to enable the two ends thereof to connect respectively into the first annular section and the third annular section; and
    a fixing bar, configured with a first rod and a second rod in a manner that the first rod is formed with a diameter about equal to the internal diameter of the second annular section of the sleeve, and the second rod is formed with a diameter about equal to the internal diameter of the third annular section of the sleeve, while allowing the first rod to fit into the second annular section of the sleeve and simultaneously allowing an end of the second rod that is disposed neighboring to the first rod to be removably inset and fixed inside the third annular section of the sleeve;
    wherein, said silicon plug both a) prevents an overflow of contrast agent/medicine when filling said cavity with said contrast agent/medicine using a first needle, and b) allows a gas exhaustion to occur, thereby enabling the internal pressure inside the cavity to become equal with the pressure outside the cavity by using a second needle simultaneously with the first needle.

2. The lesion phantom of claim 1, wherein the cavity of the lesion phantom is formed as a sphere.

3. The lesion phantom of claim 1, wherein the internal diameter of the second annular section is formed by a tapering from the first annular section toward the third annular section, and consequently, the first rod is formed in a shape conforming to the tapering of the second annular section.

4. The lesion phantom of claim 1, wherein the second rod of the fixing bar is a retractable rod.

* * * * *